(12) United States Patent
Broome et al.

(10) Patent No.: US 7,029,440 B2
(45) Date of Patent: Apr. 18, 2006

(54) DISTAL PROTECTION FILTER AND METHOD OF MANUFACTURE

(75) Inventors: Thomas E. Broome, Shakopee, MN (US); James M. Anderson, Rockford, MN (US); Robert L. Cassell, Otsego, MN (US); Verivada (Chandru) Chandrasekaran, Mercer Island, WA (US); John M. K. Daniel, Fremont, CA (US); Bradley F. Slaker, Greenfield, MN (US); Jeffrey H. Vogel, Brooklyn Park, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 395 days.

(21) Appl. No.: 10/099,219

(22) Filed: Mar. 13, 2002

(65) Prior Publication Data

US 2003/0176885 A1 Sep. 18, 2003

(51) Int. Cl.
*A61M 29/00* (2006.01)
(52) U.S. Cl. .................................................... 600/200
(58) Field of Classification Search ................ 606/200, 606/127; 623/901; 264/299
See application file for complete search history.

(56) References Cited

U.S. PATENT DOCUMENTS

| 3,472,230 | A |   | 10/1969 | Fogarty |
|---|---|---|---|---|
| 3,952,747 | A |   | 4/1976 | Kimmell, Jr. |
| 3,996,938 | A |   | 12/1976 | Clark, III |
| 4,046,150 | A |   | 9/1977 | Schwartz et al. |
| 4,425,908 | A | * | 1/1984 | Simon ........................ 606/200 |
| 4,590,938 | A |   | 5/1986 | Segura et al. |
| 4,619,246 | A |   | 10/1986 | Molgaard-Nielsen et al. |
| 4,650,466 | A |   | 3/1987 | Luther |
| 4,706,671 | A |   | 11/1987 | Weinrib |
| 4,723,549 | A |   | 2/1988 | Wholey et al. |
| 4,790,812 | A |   | 12/1988 | Hawkins, Jr. et al. |
| 4,790,813 | A |   | 12/1988 | Kensey |
| 4,794,928 | A |   | 1/1989 | Kletschka |
| 4,807,626 | A |   | 2/1989 | McGirr |
| 4,842,579 | A |   | 6/1989 | Shiber |
| 4,873,978 | A |   | 10/1989 | Ginsburg |
| 4,921,478 | A |   | 5/1990 | Solano et al. |
| 4,921,484 | A |   | 5/1990 | Hillstead |
| 4,926,858 | A |   | 5/1990 | Gifford, III et al. |
| 4,969,891 | A |   | 11/1990 | Gewertz |
| 4,998,539 | A |   | 3/1991 | Delsanti |
| 5,002,560 | A |   | 3/1991 | Machold et al. |
| 5,011,488 | A |   | 4/1991 | Ginsburg |
| 5,053,008 | A |   | 10/1991 | Bajaj |
| 5,071,407 | A |   | 12/1991 | Termin et al. |
| 5,100,423 | A |   | 3/1992 | Fearnot |
| 5,102,415 | A |   | 4/1992 | Guenther et al. |

(Continued)

FOREIGN PATENT DOCUMENTS

DE 28 21 048 7/1980

(Continued)

OTHER PUBLICATIONS

"Atherosclerotic Disease of the Aortic Arch as a Risk Factor of Recurrent Ischemic Stroke," *The New England Journal of Medicine*, pp. 1216-1221 (May 1996).

(Continued)

*Primary Examiner*—Julian W. Woo
*Assistant Examiner*—Sarah K Webb
(74) *Attorney, Agent, or Firm*—Crompton, Seager & Tufte LLC

(57) ABSTRACT

Distal protection filter frame and method for using and manufacturing the same. A distal protection filter frame may include one or more struts, a mouth, and a filter coupled to the mouth.

1 Claim, 8 Drawing Sheets

U.S. PATENT DOCUMENTS

| | | | |
|---|---|---|---|
| 5,133,733 | A | 7/1992 | Rasmussen et al. |
| 5,152,771 | A | 10/1992 | Sabbaghian et al. |
| 5,152,777 | A | 10/1992 | Goldberg et al. |
| 5,160,342 | A | 11/1992 | Reger et al. |
| 5,224,953 | A | 7/1993 | Morgentaler |
| 5,324,304 | A | 6/1994 | Rasmussen |
| 5,329,942 | A | 7/1994 | Gunther et al. |
| 5,330,484 | A | 7/1994 | Gunther |
| 5,354,310 | A | 10/1994 | Garnie et al. |
| 5,376,100 | A | 12/1994 | Lefebvre |
| 5,421,832 | A | 6/1995 | Lefebvre |
| 5,423,742 | A | 6/1995 | Theron |
| 5,449,372 | A | 9/1995 | Schmaltz et al. |
| 5,456,667 | A | 10/1995 | Ham et al. |
| 5,462,529 | A | 10/1995 | Simpson et al. |
| 5,536,242 | A | 7/1996 | Willard et al. |
| 5,549,626 | A | 8/1996 | Miller et al. |
| 5,658,296 | A | 8/1997 | Bates et al. |
| 5,662,671 | A | 9/1997 | Barbut et al. |
| 5,695,519 | A | 12/1997 | Summers et al. |
| 5,713,853 | A * | 2/1998 | Clark et al. ............... 606/200 |
| 5,713,949 | A * | 2/1998 | Jayaraman ............... 623/1.12 |
| 5,720,764 | A | 2/1998 | Naderlinger |
| 5,728,066 | A | 3/1998 | Daneshvar |
| 5,749,848 | A | 5/1998 | Jang et al. |
| 5,769,816 | A | 6/1998 | Barbut et al. |
| 5,779,716 | A | 7/1998 | Cano et al. |
| 5,792,157 | A | 8/1998 | Mische et al. |
| 5,795,322 | A | 8/1998 | Bouewijn |
| 5,800,457 | A | 9/1998 | Gelbfish |
| 5,800,525 | A | 9/1998 | Bachinski et al. |
| 5,810,874 | A | 9/1998 | Lefebvre |
| 5,814,064 | A | 9/1998 | Daniel et al. |
| 5,827,324 | A | 10/1998 | Cassell et al. |
| 5,833,644 | A | 11/1998 | Zadno-Azizi et al. |
| 5,833,650 | A | 11/1998 | Imran |
| 5,846,260 | A | 12/1998 | Maahs |
| 5,848,964 | A | 12/1998 | Samuels |
| 5,876,367 | A | 3/1999 | Kaganov et al. |
| 5,895,399 | A | 4/1999 | Barbut et al. |
| 5,910,154 | A | 6/1999 | Tsugita et al. |
| 5,911,734 | A | 6/1999 | Tsugita et al. |
| 5,925,016 | A | 7/1999 | Chornenky et al. |
| 5,925,060 | A | 7/1999 | Forber |
| 5,925,062 | A | 7/1999 | Purdy |
| 5,935,139 | A | 8/1999 | Bates |
| 5,941,869 | A | 8/1999 | Patterson et al. |
| 5,941,896 | A | 8/1999 | Kerr |
| 5,947,995 | A | 9/1999 | Samuels |
| 5,954,745 | A | 9/1999 | Gertler et al. |
| 5,980,555 | A | 11/1999 | Barbut et al. |
| 5,989,281 | A | 11/1999 | Barbut et al. |
| 5,993,469 | A | 11/1999 | McKenzie et al. |
| 5,997,557 | A | 12/1999 | Barbut et al. |
| 6,001,118 | A | 12/1999 | Daniel et al. |
| 6,007,557 | A | 12/1999 | Ambrisco et al. |
| 6,010,522 | A | 1/2000 | Barbut et al. |
| 6,013,085 | A | 1/2000 | Howard |
| 6,027,520 | A | 2/2000 | Tsugita et al. |
| 6,042,598 | A | 3/2000 | Tsugita et al. |
| 6,051,014 | A | 4/2000 | Jang |
| 6,051,015 | A | 4/2000 | Maahs |
| 6,053,932 | A | 4/2000 | Daniel et al. |
| 6,059,814 | A | 5/2000 | Ladd |
| 6,066,149 | A | 5/2000 | Samson et al. |
| 6,066,158 | A | 5/2000 | Engelson et al. |
| 6,068,645 | A | 5/2000 | Tu |
| 6,086,605 | A | 7/2000 | Barbut et al. |
| 6,117,154 | A | 9/2000 | Barbut et al. |
| 6,129,739 | A | 10/2000 | Khosravi |
| 6,136,016 | A | 10/2000 | Barbut et al. |
| 6,142,987 | A | 11/2000 | Tsugita |
| 6,152,946 | A | 11/2000 | Broome et al. |
| 6,165,200 | A | 12/2000 | Tsugita et al. |
| 6,168,579 | B1 | 1/2001 | Tsugita |
| 6,171,327 | B1 | 1/2001 | Daniel et al. |
| 6,171,328 | B1 | 1/2001 | Addis |
| 6,179,851 | B1 | 1/2001 | Barbut et al. |
| 6,179,859 | B1 | 1/2001 | Bates et al. |
| 6,179,861 | B1 | 1/2001 | Khosravi et al. |
| 6,203,561 | B1 | 3/2001 | Ramee et al. |
| 6,206,868 | B1 | 3/2001 | Parodi |
| 6,214,026 | B1 | 4/2001 | Lepak et al. |
| 6,221,006 | B1 | 4/2001 | Dubrul et al. |
| 6,224,620 | B1 | 5/2001 | Maahs |
| 6,231,544 | B1 | 5/2001 | Tsugita et al. |
| 6,235,044 | B1 | 5/2001 | Root et al. |
| 6,235,045 | B1 | 5/2001 | Barbut et al. |
| 6,238,412 | B1 | 5/2001 | Dubrul et al. |
| 6,245,087 | B1 | 6/2001 | Addis |
| 6,245,088 | B1 | 6/2001 | Lowery |
| 6,245,089 | B1 | 6/2001 | Daniel et al. |
| 6,258,115 | B1 | 7/2001 | Dubrul |
| 6,264,663 | B1 | 7/2001 | Cano |
| 6,264,672 | B1 | 7/2001 | Fisher |
| 6,270,513 | B1 | 8/2001 | Tsugita et al. |
| 6,277,138 | B1 | 8/2001 | Levinson et al. |
| 6,277,139 | B1 | 8/2001 | Levinson et al. |
| 6,280,413 | B1 | 8/2001 | Clark et al. |
| 6,287,321 | B1 | 9/2001 | Jang |
| 6,290,710 | B1 | 9/2001 | Cryer et al. |
| 6,309,399 | B1 | 10/2001 | Barbut et al. |
| 6,319,268 | B1 | 11/2001 | Ambrisco et al. |
| 6,344,049 | B1 | 2/2002 | Levinson et al. |
| 6,346,116 | B1 | 2/2002 | Brooks et al. |
| 6,494,909 | B1 * | 12/2002 | Greenhalgh ............... 623/1.24 |
| 6,565,599 | B1 * | 5/2003 | Hong et al. ............... 623/1.15 |
| 2002/0004667 | A1 * | 1/2002 | Adams et al. ............... 606/200 |

FOREIGN PATENT DOCUMENTS

| | | |
|---|---|---|
| DE | 34 17 738 | 11/1985 |
| DE | 40 30 998 A1 | 10/1990 |
| DE | 199 16 162 | 10/2000 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 0 934 729 | 8/1999 |
| EP | 1 127 556 A2 | 8/2001 |
| FR | 2 580 504 | 10/1986 |
| FR | 2 643 250 A1 | 8/1990 |
| FR | 2 666 980 | 3/1992 |
| FR | 2 694 687 | 8/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |

| | | |
|---|---|---|
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01/62184 A2 | 8/2001 |
| WO | WO 01/67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |

OTHER PUBLICATIONS

"Endovascular Grafts, Stents Drive Interventional Radiology Growth," *Cardiovascular Device Update*, 2(3):1-12 (Mar. 1996).

"Protruding Atheromas in the Thoracic Aortic and Systemic Embolization," pp. 423-427 *American College of Physicians* (1991).

"Recognition and Embolic Potential of Intraaortic Atherosclerotic Debris," *American College of Cardiology* (Jan. 1991).

Cragg, Andrew et al., "A New Percutaneous Vena Cava Filger," *AJR*, 141:601-604 (Sep. 1983).

Cragg, Andrew et al., "Nonsurgical Placement of Arterial Endoprosthesis: A New Technique Using Nitinol Wire," *AJR*, pp. 261-263 (Apr. 1983).

Dietbrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during the course of cardiac surgery," *Surgery*, 64(3):634-639 (Sep. 1968).

Haissaguerre et al., "Spontaneous Initiation of Atrial Fibrillation by Ectopic Beats Originating in the Pulmonary Veins," *The New England Journal of Medicine*, 339(10):659-666 (Sep. 1988).

Jordan, Jr. et al., "Microemboli Detected by Transcranial Doppler Monitoring . . . ," *Cardiovascular Surgery*, 7(1)33-38 (Jan. 1999).

Lesh, "Can Catheter Ablation Cure Atrial Fibrillation?" *ACC Current Journal Review*, pp. 38-40 (Sep./Oct. 1997).

Lund et al., "Long-Term Patentcy of Ductus Arteriosus After Balloon Dilation: an Experimental Study," *Laboratory Investigation*, 69(4):772-774 (Apr. 1984).

Marache et al., "Percutaneous Transluminal Venous Angioplasty . . . ," *American Heart Journal*, 125(2 Pt 1):362-366 (Feb. 1993).

Mazur et al., "Directional Atherectomy with the Omnicath™: A Unique New Catheter System," *Catheterization and Cardiovascular Diagnosis*, 31:17-84 (1994).

Moussa, MD, Issaam "Stents Don't Require Systemic Anticoagulation . . . But the Technique (and Results) Must be Optimal," *Journal of Invasive Cardiol.*, 8(E):3E-7E, (1996).

Nakanishi et al., "Catheter Intervention to Venous System Using Expandable Metallic Stents," *Rinsho Kyobu Geka*, 14(2):English Abstract Only (Apr. 1994).

Onal et al., "Primary Stenting for Complex Atherosclerotic Plaques in Aortic and Iliac Stenoses," *Cardiovascular & Interventional Radiology*, 21(5):386-392 (1998).

Theron et al., "New Triple Coaxial Catheter System for Carotid Angioplasty with Cerebral Protection," *American Journal of Neuroradiology*, 11:869-874 (1990).

Tunick et al., "Protruding atherosclerotic plaque in the aortic archo f patients with systemic embolization: A new finding seen by transesophageal echocardiography," *American Heart Journal* 120(3):658-660 (Sep. 1990).

Waksman et al., "Distal Embolization is Common After Directional Atherectomy . . . ," *American Heart Journal*, 129(3):430-435 (1995).

Wholey, Mark H. et al., PTA and Stents in the Treatment of Extracranial Circulation, *The Journal of Invasive Cardiology*, 8(E):25E-30E (1996).

* cited by examiner

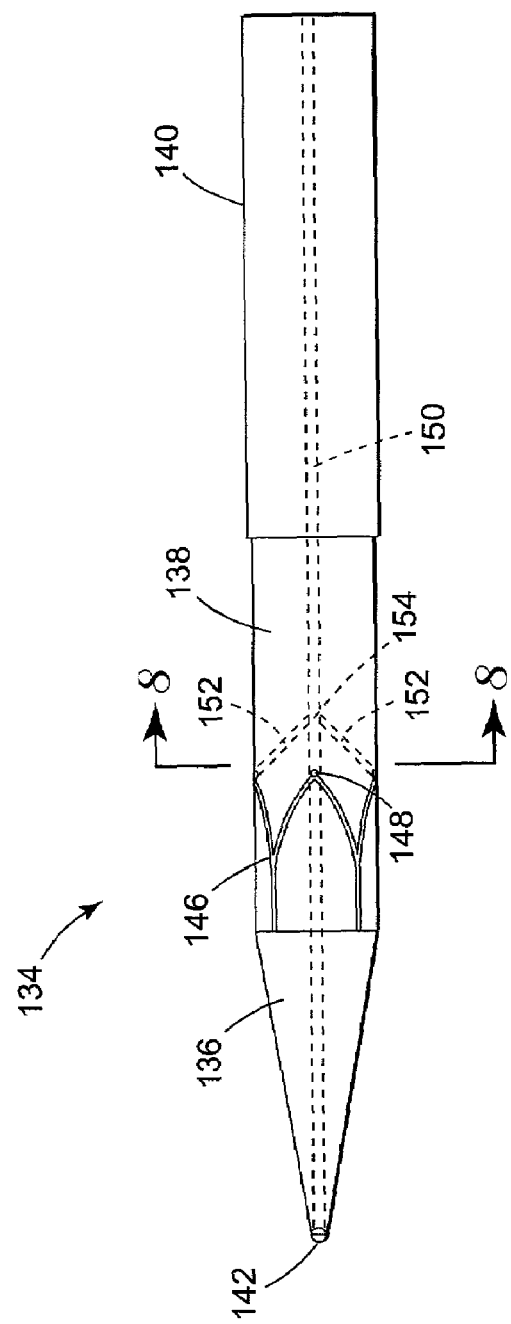
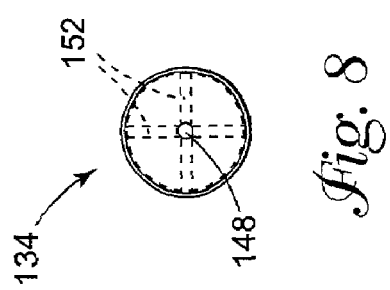
Fig. 7
Fig. 8

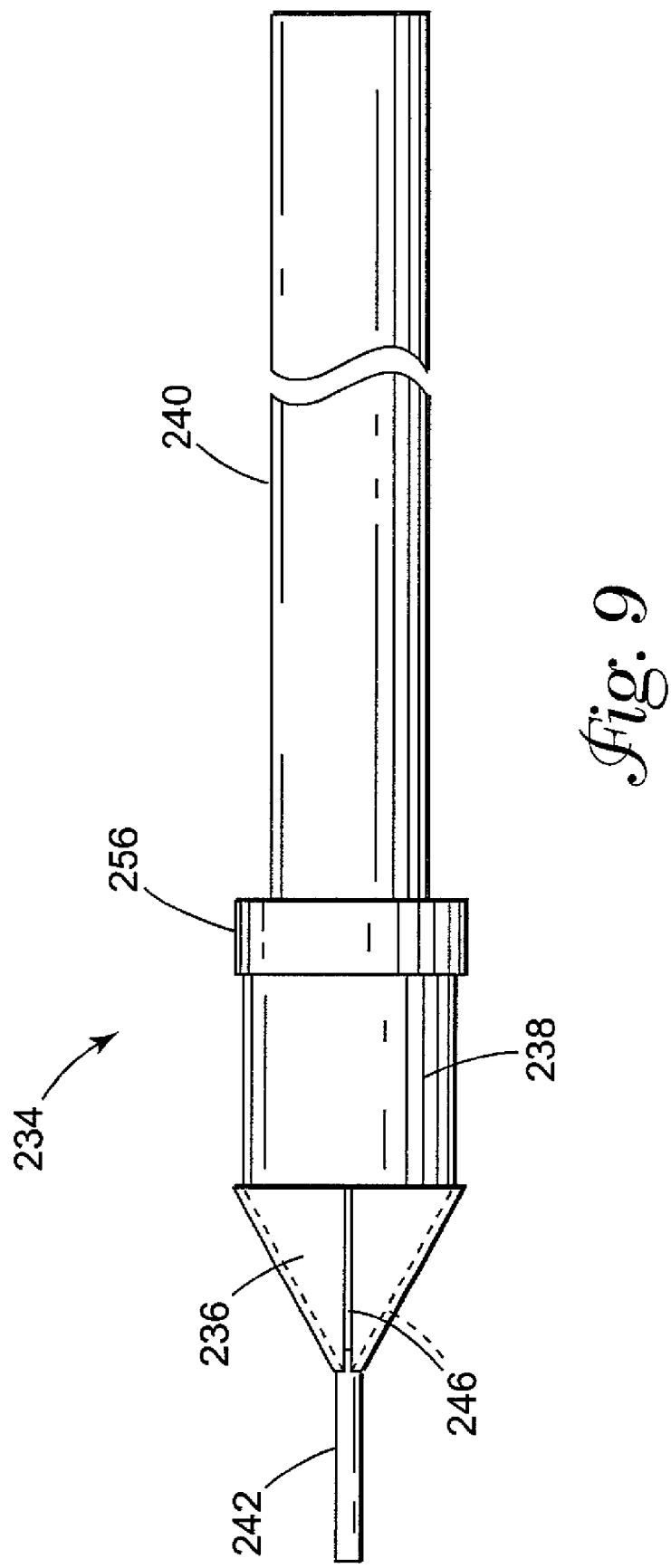

DISTAL PROTECTION FILTER AND METHOD OF MANUFACTURE

BACKGROUND OF THE INVENTION

1. Field of the Invention

The present invention pertains to distal protection catheters for filtering embolic debris. More precisely, the present invention pertains to distal protection filters including a refinement to the filter frame.

2. Description of the Related Art

Heart disease is a major problem in the United States and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire such that the balloon is positioned adjacent a stenotic lesion. The balloon is then inflated and the restriction of the vessel is opened. During an atherectomy procedure, the stenotic lesion may be mechanically cut away from the blood vessel wall using an atherectomy catheter.

During angioplasty and atherectomy procedures, embolic debris can be separated from the wall of the blood vessel. If this debris enters the circulatory system, it could block other vascular regions including the neural and pulmonary vasculature, both of which are highly undesirable. During angioplasty procedures, stenotic debris may also break loose due to manipulation of the blood vessel. Because of this debris, a number of devices, termed distal protection devices, have been developed to filter out this debris.

BRIEF SUMMARY OF THE INVENTION

The present invention pertains to distal protection filter assemblies. More particularly, the present invention pertains to distal protection filter frames. A filter frame may include a plurality of struts or ribs and a crown or mouth portion. The crown portion may be adapted and configured to have a distal protection filter coupled thereto.

A number of different mandrels may be used to manufacture the filter frame. For example, a mandrel may include a proximal region, a distal region, and a middle region. In addition, the mandrel may include grooves for holding the filter frame in place. Further, the mandrel may include openings leading to a guidewire channel or a screw dip rod.

BRIEF DESCRIPTION OF THE SEVERAL VIEWS OF THE DRAWINGS

FIG. 7 is a perspective view of an alternate mandrel for use in forming a distal protection filter frame;

FIG. 8 is a cross sectional view taken through line 7—7 of the mandrel shown in FIG. 7; and FIG. 9 is a perspective view of a second alternate mandrel for use in forming a distal protection filter frame.

DETAILED DESCRIPTION OF THE INVENTION

Figure 1:
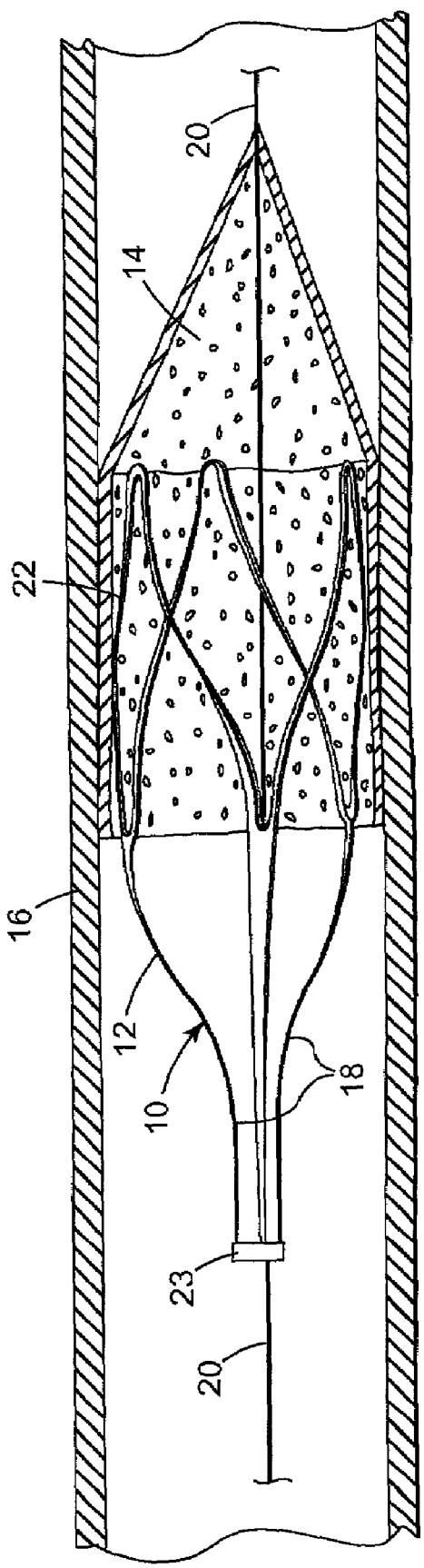
FIG. 1 is a cross sectional view of a distal protection filter disposed within the vasculature of a patient.

The following description should be read with reference to the drawings wherein like reference numerals indicate like elements throughout the several views. The detailed description and drawings illustrate example embodiments of the claimed invention.

FIG. 1 is a cross sectional view of a distal protection filter disposed within the vasculature of a patient. When performing any one of a number of differing intravascular procedures, embolic debris may drift away from the treatment site and, potentially, obstruct downstream vascular regions. These obstructions could lead to adverse medical conditions and/or tissue damage. A strategy that may help prevent embolic debris from causing problems downstream of an intravascular procedure may include the use of a distal protection filter 10. Distal protection filter 10 includes a filter frame 12 having a filter material 14 coupled thereto.

Filter frame 12 may be comprised of metal such as nickel-titanium alloy or stainless steel and configured to have one or more struts 18 coupled to an elongate shaft or guidewire 20, and a crown defining mouth portion 22 coupled to filter material 14. Frame 12 may be self-expanding so that frame 12 will expand to engage and generally conform to the internal lumen a blood vessel 16 when being delivered (e.g., from a delivery catheter or sheath).

Distal protection filter material 14 may be coupled to guidewire 20 proximate a distal end of guidewire 20. Filter material 14 and guidewire 20 may generally comprise a number of configurations known to those skilled in the appropriate art. Filter material 14 may be comprised of a polyurethane sheet and include at least one opening that may be, for example, formed by known laser techniques. The holes or openings are sized to allow blood flow therethrough but restrict flow of debris or emboli floating in the body lumen or cavity.

Filter 10 may be generally cone-shaped, and have a proximal and a distal end. The distal end may be a narrow, "V"-shaped end and is secured to guidewire 20 and/or frame 12. Alternatively, filter 10 may be cylindrical with a relatively rounded distal end. Filter 10 operates between a closed collapsed profile and an open radially-expanded deployed profile for collecting debris in a body lumen. In an expanded profile, the mouth is opened and struts 18 extend radially outwardly to support the mouth. Struts 18 may be coupled to guidewire 20 by a strut coupling member 23. A number of differing configurations of filter material 14 may be substituted without departing from the spirit of the invention.

In addition, a portion of frame 12 may be comprised of or plated with radiopaque materials. Radiopaque materials are understood to be capable of producing a relatively bright image on a fluoroscopy screen or another imaging technique during an intravascular procedure. This relatively bright image aids the user of distal protection assembly 10 in determining the location of frame 12 with respect to the patient's vascular anatomy. Radiopaque materials may include, but are not limited to, gold, platinum, tungsten alloy, and plastic material loaded with a radiopaque filler.

Figure 2:
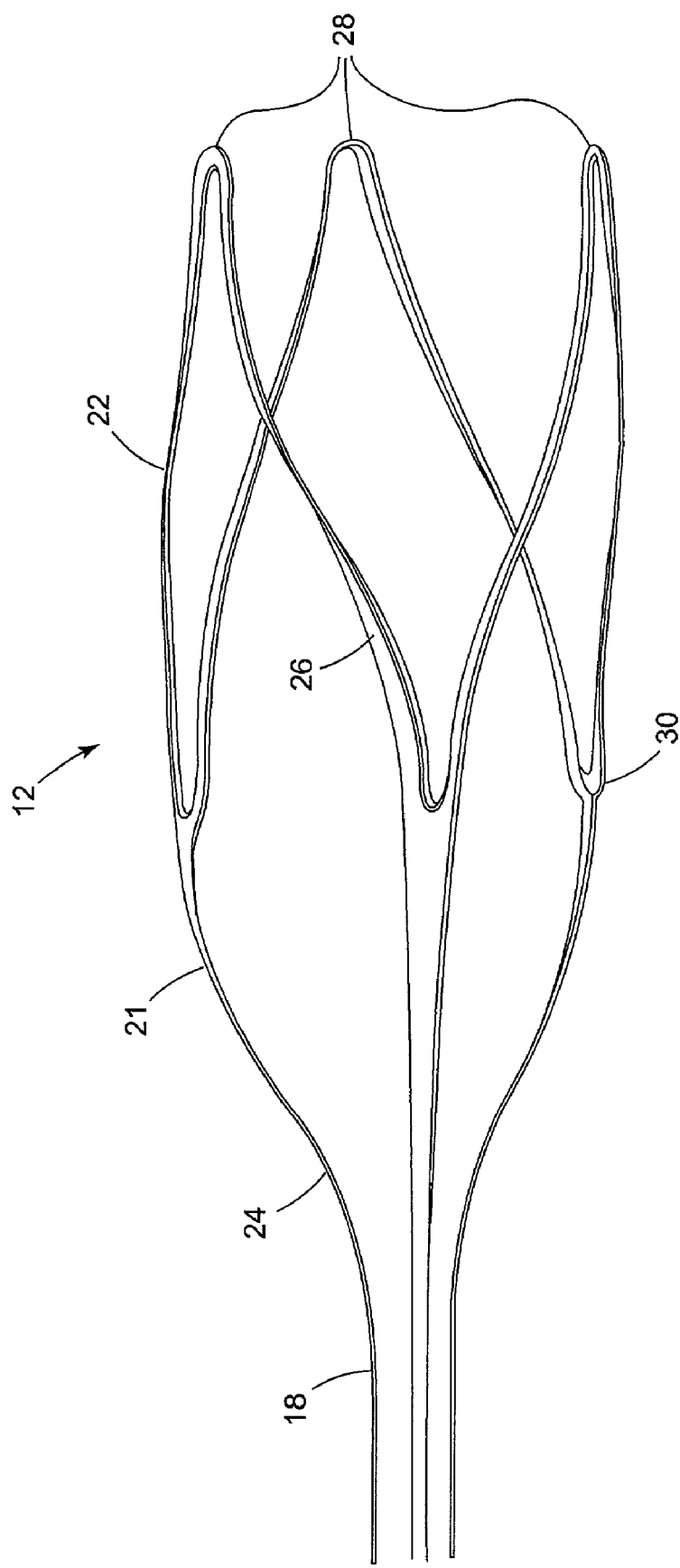
FIG. 2 is a perspective view of a filter frame for use with a distal protection filter.

FIG. 2 is a perspective view of filter frame 12 for use with distal protection filter material 14. A number of features may be incorporated into filter frame 12. For example, filter frame 12 may be constructed with a geometry that is optimized for essentially complete apposition to the internal wall of blood vessel 16 (i.e., frame 12 conforms to the shape of blood vessel 16) and minimal peak strains within frame 12. Peak strain is understood to be strain at points along frame 12 where force is concentrated. Therefore, peak strain may be minimized by distributing the force evenly throughout frame 12. In addition, frame 12 includes a greater expansion ratio. Expansion ratio is understood to be the ratio of the diameter (or area) of frame 12 between an expanded configuration and a collapsed configuration. Increasing the expansion ratio may allow frame 12 to be collapsed to a generally small profile and still be capable of expanding to conform to the size of a blood vessel. These and other features may allow frame 12 to be delivered with a small profile.

Struts or ribs 18 may be pre-curved during manufacturing to include a first curved portion 24. When frame 12 is collapsed within a delivery sheath, stress on frame 12 may longitudinally deform or strain frame 12. Curved portion 24 has a constant radius so that when frame 12 is collapsed, stress and/or strain forces are evenly distributed longitudinally throughout frame 12. According to this embodiment, the peak strain within struts 18 and/or frame 12 when frame 12 may be minimized by including curved portion 24.

Struts 18 and crown portion 22 may be continuous and be joined by a second curved portion 26. Similarly to curved portion 24, portion 26 is also curved to minimize peak strain near crown portion 26. However, the radius of curvature of curved portion 26 may be variable or include portions where the radius varies. In addition, crown portion 22 extends between a distal end 28 and a plurality of strut intersection points 30. Struts 18 may extend from points 30 and be coupled to guidewire 20.

It should be noted that the number of struts 18 and points 30 can be altered without departing from the scope of the present invention. For example, frame 12 may include two, three, four, five, six, or more points. It is believed that increasing the number of struts 18 and/or points 30 would decrease the expansion ratio of frame 12. For example, increasing the number of points 30 from four to six would increase the inside diameter of frame 12. Different diameter sizes may be favored when performing an intravascular procedure within different blood vessels.

Figure 3:
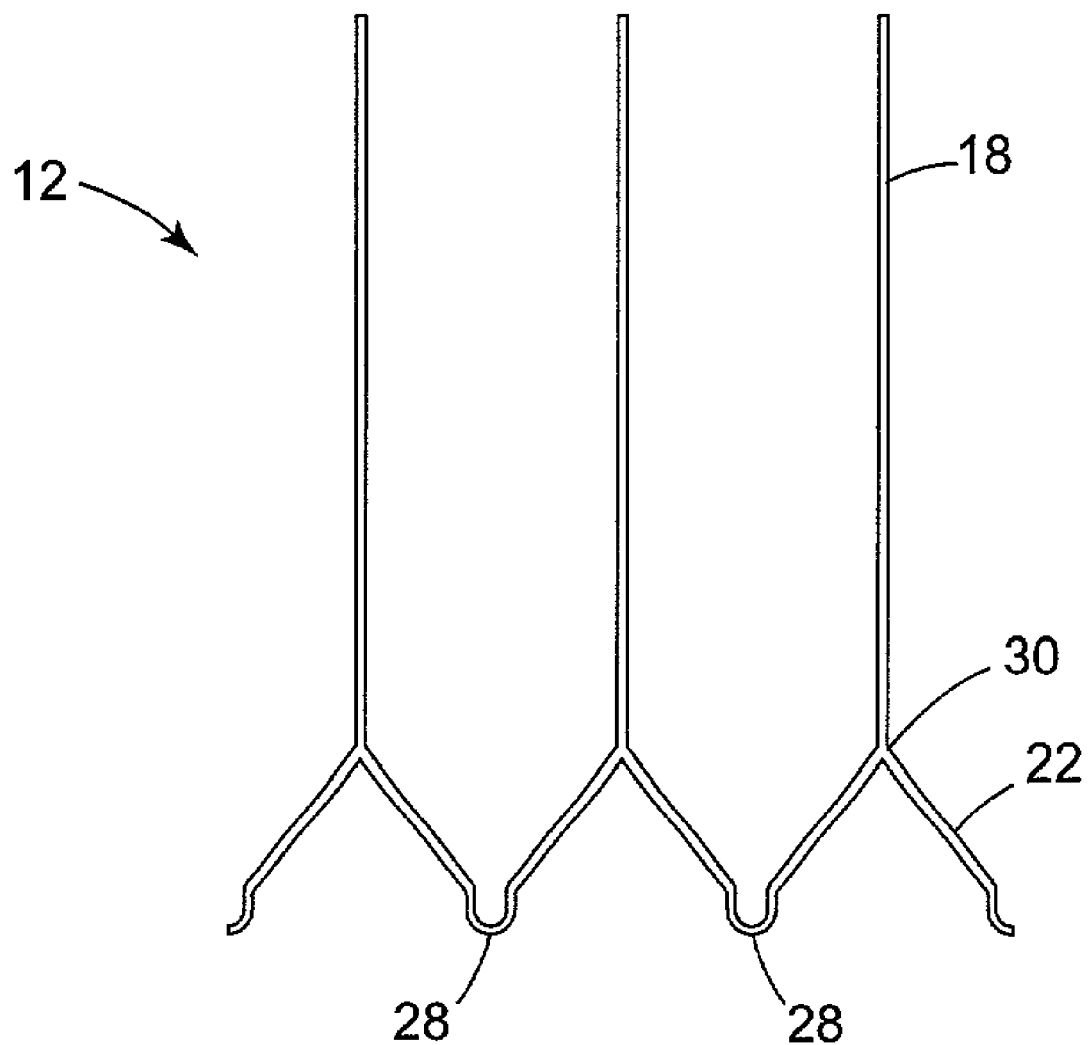
FIG. 3 is a flattened plan view of the filter frame.

FIG. 3 is a flattened plan view of distal protection filter frame 12. When manufacturing frame 12 it may be beneficial to first manufacture a planar version of the appropriate material (e.g., nickel-titanium alloy). The planar version may be formed into the desired shape by disposing frame 12 about a mandrel (examples are shown below in FIGS. 6–9) and coupling opposite ends together, for example by soldering or welding.

Figure 4:
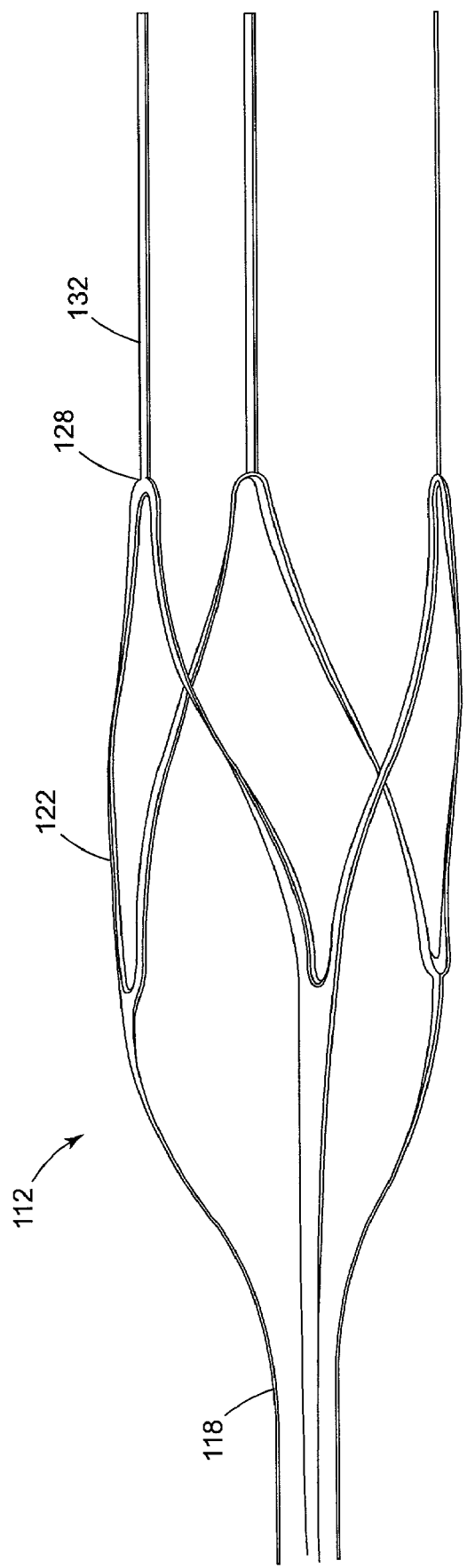
FIG. 4 is a perspective view of an alternate filter frame for use with a distal protection filter.

FIG. 4 is a perspective view of an alternate filter frame 112 for use with distal protection filter material 14. Frame 112 is essentially the same in form and function as frame 12 in that frame 112, except that frame 112 further comprises distally-oriented struts 132 in addition to struts 118. Distally-oriented struts 132 extend distally between distal end 128 of crown portion 122 and guidewire 20.

Struts 132 provide additional support for filter material 14. According to this embodiment, when frame 12 is coupled to filter material 14, struts 132 may be adapted and configured to follow the contour of filter material 14 and provide structural support along the length thereof. At a distal end, struts 132 may be coupled to the distal end of filter material 14 and/or be coupled to guidewire 20. Similarly to FIG. 3, FIG. 5 is a flattened plan view filter frame 112.

Figure 6:
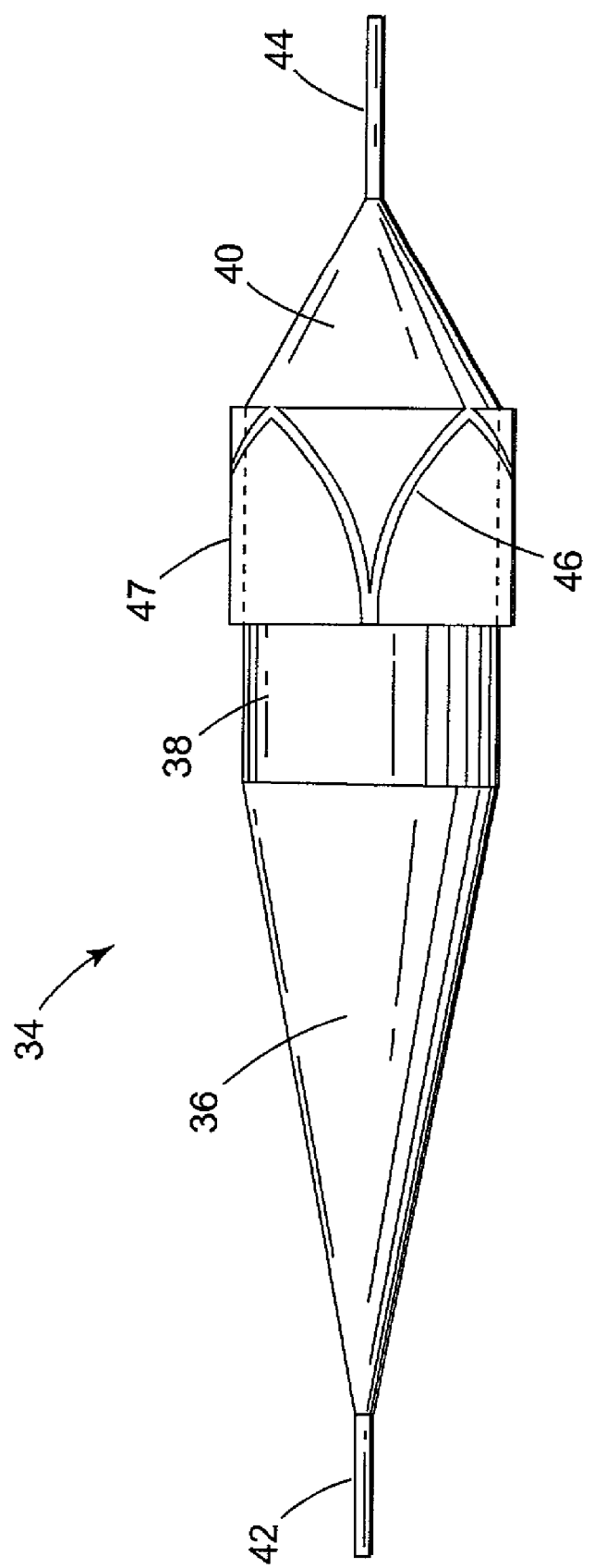
FIG. 6 is a perspective view of a mandrel for use in forming a distal protection filter frame.

FIG. 6 is a perspective view of a mandrel 34 for use in manufacturing a distal protection filter frame (e.g., frame 12 and frame 112). Mandrel 34 includes a generally tapered or cone-like distal region 36, a middle region 38, and a tapered proximal region 40. In addition, mandrel 34 may include a distal tip 42 and a proximal tip 44 disposed proximate their respective regions. It should be appreciated that although the subsequent discussion is focused upon frame 12 it is similarly applicable to frame 112

Middle region 38 includes grooves 46 adapted and configured for holding at least a portion of filter frame 12. Grooves 46 are curved such that disposing crown portion 22 within grooves 46 may lead to the formation of second curved portion 26. In addition, the transition from the relatively straight middle region 38 to the tapered proximal region 40 may lead to the formation of first curved portion 24, although pre-curving may be desirable if the transition between proximal region 40 and middle region 38 bends more sharply than desired.

Figure 5:
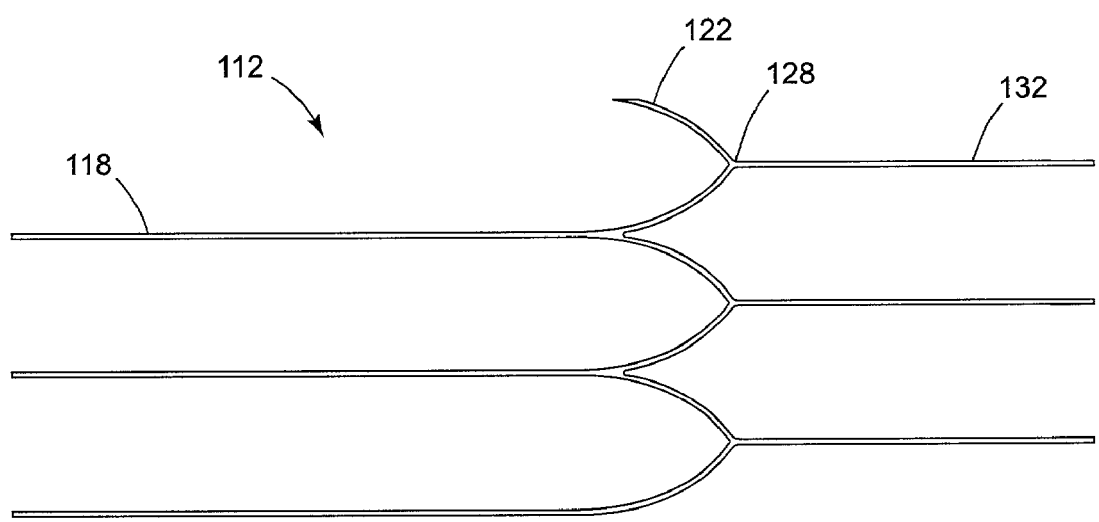
FIG. 5 is a flattened plan view of the alternate distal protection filter frame.

In use, the planar configurations shown in FIGS. 3 and 5 of frame 12 (and/or frame 112) may be disposed about mandrel 34 such that crown portion 22 or 122 is disposed within groove 46. Struts 18 may extend between middle region 38 and proximal region 40 wherein the transition between regions tapers struts 18 toward the center and can be used to form first curve 24. The proximal ends of struts 18 may be disposed near proximal tip 44 where they may be coupled to guidewire 20. A collar 47 may be slidably disposed along middle region 38 that is adapted and configured to be slid over struts 18 and/or crown portion 22 (or crown portion 122) to hold frame 12 in position. Once held in position, the shape of frame 12 may be set to conform to the shape of the mandrel using methods described below or those known in the art. Following shape setting, frame 12 can be removed from mandrel 34 or it may be coupled with filter material 14, for example by dipping distal region 36 into molten or partially molten filter material 14.

Heat setting may be used to set the shape of frame 12 (and frame 112). For example, frame 12 may be comprised of a shape memory alloy that can be heat set. Thus, frame 12 may be disposed about mandrel 34 and heated to set the shape of frame 12 to conform to the shape of mandrel 34. According to this embodiment, mandrel 34 (and subsequently described mandrels) may be comprised of materials that would resist heat deformation such as stainless steel. Once heat set, frame 12 deformed to an alternate shape will return to the heat set shape after force used to deform frame 12 is removed. It may be desirable to heat set frame 12 in the expanded configuration such that delivery of filter 10 from within a relatively small delivery sheath permits frame 12 to self-expand when the delivery sheath is withdrawn.

It should be noted that mandrel 34 may be hollow such that guidewire 20 may pass therethrough with opposing end extending from distal tip 42 and proximal tip 44. This embodiment may simplify the process of coupling struts 18 (or struts 132) to guidewire 20 if desired by establishing proper alignment. This step may similarly achieved independently of mandrel 34.

When used for frame 112, the above steps occur analogously to what is described above. In addition, struts 132 extend between middle region 38 and distal region 36 wherein struts 132 taper toward the center. The distal ends of struts 132 may be disposed near distal tip 42 where they may be coupled to guidewire 20.

Once frame 12 or 112 is properly configured, filter material 14 may be coupled thereto. For example, suitable filter materials may be molten or partially molten and frame 12 or 112 may be coupled to filter material 14 by dipping distal region 36 (or 136) into the suitable filter materials 14 as described above. It should be appreciated that a person of ordinary skill in the art would be familiar with suitable filter materials and method for coupling filter material 14 to frame 12.

FIG. 7 is a perspective view of an alternate mandrel 134 for use in forming a distal protection filter frame. Mandrel 134 is similar to mandrel 34 in that it includes distal region 136, middle region 138, proximal region 140, distal tip 142, and grooves 146. In addition, middle region 138 of mandrel 134 include one or more openings 148 to a guidewire channel 150. Openings 148 may be used for shaping struts or be a place for struts to extending during formation of the filter frame. According to this embodiment, a filter frame may be configured such that struts or ribs 18 pass through openings 148, into a strut channel 152 and come together at an apex 154. Openings 148 may be useful for tapering struts 18 toward guidewire 20. Other than the differences noted above, use of mandrel 134 may be similar to that of mandrel 34. FIG. 8 is a cross sectional view taken through line 7—7 of the mandrel shown in FIG. 7 showing channels 152.

FIG. 9 is a perspective view of a second alternate mandrel 234 for use in forming a distal protection filter frame. Mandrel 234 is similar to mandrel 34 in form and function in that it includes distal region 236, middle region 238, proximal region 240, distal tip 242, and grooves 246. In addition, middle region 238 of mandrel 234 includes a screw dip rod 256.

Filter frame 112 may be coupled to mandrel 234 such that crown portion 122 is disposed about middle region 238 and struts 132 are disposed within grooves 246 and extend toward distal tip 242. Screw dip rod 256 may be actuated so as to pass over and hold or set the shape of crown portion 122 into a generally circular configuration. Then, heat may be used to set the shape similarly to what is described above. Struts 132 may be coupled to guidewire 20 that may pass through mandrel 234 and exit therefrom at distal tip 242. Filter material 14 may be formed in a manner similar to what is described above.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A method of manufacturing a distal protection filter assembly, comprising the steps of:
    providing a filter frame having a plurality of struts and a filter body section;
    providing a mandrel having a longitudinal axis, a proximal region, a middle region, and a distal region, the middle region having a groove formed therein that extends about the longitudinal axis of the mandrel;
    coupling the filter frame to the mandrel wherein at least a portion of the body section is disposed within the groove;
    coupling filter material to at least a portion of the filter frame; and
    wherein the mandrel includes one or more strut channels and a guidewire channel, and wherein the step of coupling the filter frame to the mandrel includes passing the struts through the strut channels and into the guidewire channel.

* * * * *